United States Patent [19]

John

[11] Patent Number: 4,545,388
[45] Date of Patent: Oct. 8, 1985

[54] SELF-NORMED BRAIN STATE MONITORING

[76] Inventor: E. Roy John, 265 S. Barry Ave., Mamaroneck, N.Y. 10543

[21] Appl. No.: 502,568

[22] Filed: Jun. 9, 1983

[51] Int. Cl.$^4$ .............................................. A61B 5/04
[52] U.S. Cl. .................................................. 128/731
[58] Field of Search ................................ 128/731-733

[56] References Cited

U.S. PATENT DOCUMENTS

| | | | |
|---|---|---|---|
| 3,513,834 | 5/1970 | Suzuki et al. | 128/731 |
| 3,696,808 | 10/1972 | John | 128/731 |
| 3,760,796 | 9/1973 | Baessler et al. | 128/731 |
| 3,901,215 | 8/1975 | John | 128/731 |
| 4,188,956 | 2/1980 | John | 128/731 |
| 4,201,224 | 5/1980 | John | 128/731 |
| 4,214,591 | 7/1980 | Sato et al. | 128/731 |
| 4,216,781 | 8/1980 | John | 128/731 |
| 4,279,258 | 7/1981 | John | 128/731 |

Primary Examiner—Lee S. Cohen
Assistant Examiner—Angela D. Sykes
Attorney, Agent, or Firm—Eliot S. Gerber

[57] ABSTRACT

Disclosed are a method and an apparatus for monitoring the brain state of a patient during a medical procedure relative to a self-norm established at an earlier time, when the patient is in a state selected for medical relevance to the planned procedure. To establish the pre-procedure self-norm, electrical measurements are taken of brain functions which are selected for medical relevance to the procedure, and are processed to produce, for each brain function of interest, a respective statistically and medically significant mean and variance. During the procedure, the same brain functions are electrically measured at each of a sequence of time intervals selected for medical relevance to the procedure. Each new set of measurements is tested for statistically amd medically significant change from the self-norm and, if a test shows such a change, a tangible indication is produced, showing not only that a change has occurred but also showing the ascribed medical significance of the change itself and the persistence of a change.

2 Claims, 1 Drawing Figure

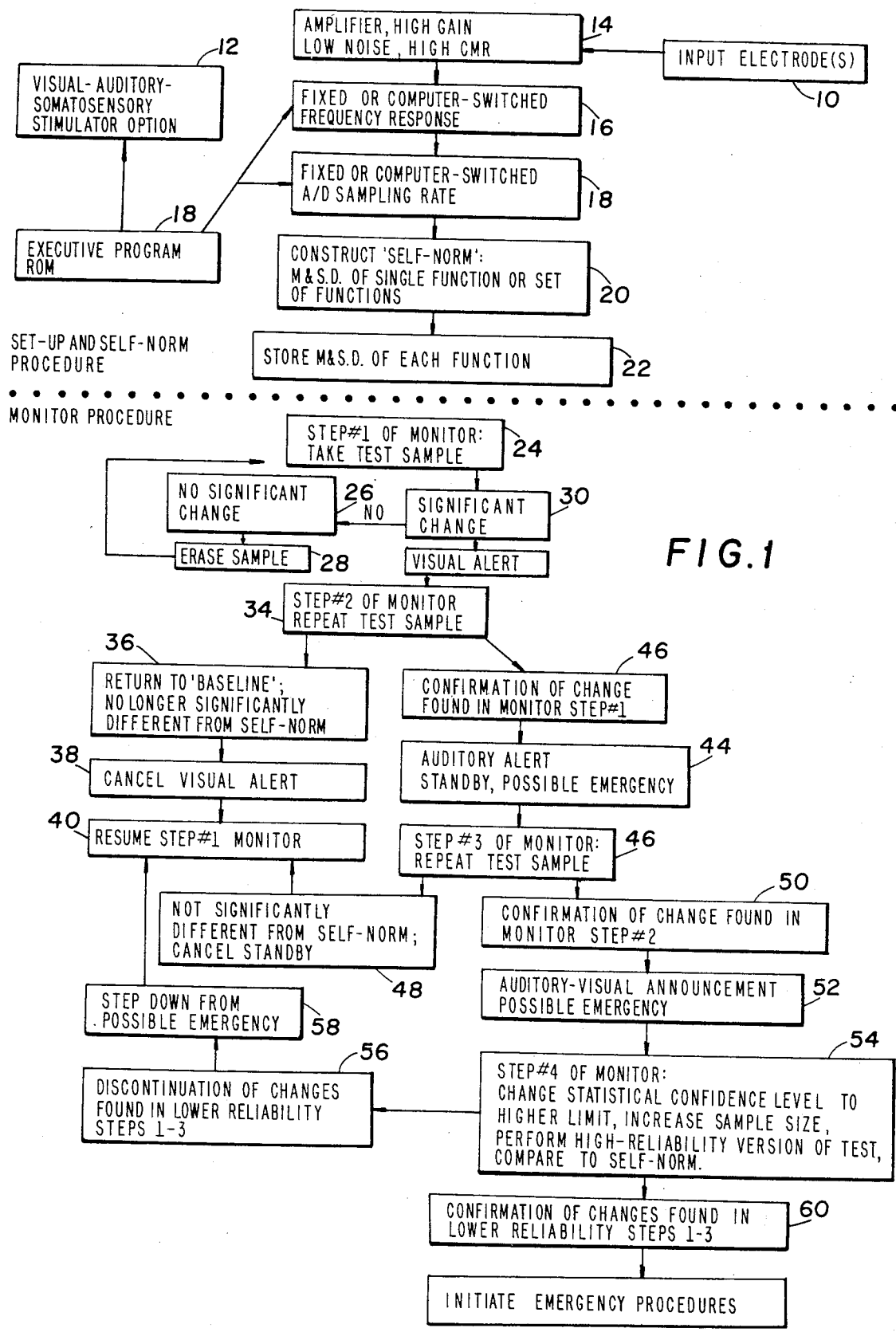

SELF-NORMED BRAIN STATE MONITORING

BACKGROUND AND SUMMARY OF THE INVENTION

The invention relates to monitoring brain function by measuring and processing time-varying spontaneous electrical potentials which exist between different areas of a patient's scalp and/or body, and/or time-varying evoked potentials produced in response to stimuli delivered to the patient.

More specific aspects of the invention relate to monitoring the occurrence and ascribed medical significance of changes in a patient undergoing a medical procedure relative to an earlier state of the patient, at a time selected for medical relevance to the planned procedure, and to producing, in case of statistically and medically significant deviations from the self-norm, alarms which convey information both as to the occurrence of such deviations and so to the ascribed medical significance of the deviation itself and its persistence. One non-limiting example is monitoring relevant brain functions of a patient undergoing surgery which has the potential of impairing the regional blood supply to the cortex, and producing suitable alarms in case of detecting medically significant blood (and oxygen) supply impairment. Numerous other examples are identified below.

It is well known that spontaneous electrical potentials (SP) exist between different areas of a patient's scalp and/or other body parts, and that a record thereof over a period of time, called an electroencephalogram, or EEG for short, can be studied in an effort to relate the SP to brain activity and function. It is also known that when a patient is subjected to stimuli, evoked potentials (EP) tend to be superimposed on the normally present EEG potentials, and that the EP waveforms can also be studied in an effort to relate them to brain activity and function. It is further well known that the SP and EP measurements produce extremely weak signals which are subject to many adverse influences and are therefore difficult to measure accurately and precisely, and that the medically significant information contained in them is typically severely obscured.

Traditionally, a clinician evaluating SP and EG measurements relies on visual inspection of raw or averaged waveforms in seeking to extract the relevant diagnostic features. Aside from depending to a great extent on the experience, skill and judgment of the particular clinician, this method is immensely complicated by the high inherent variability of the relevant waveforms. In an effort to enhance the available information, various machine-processing techniques have been applied to the raw measurements which, in addition to seeking to enhance the signal-to-noise ratio, match the information derived from a particular patient with a norm derived from a large population of persons who are believed to be "normal" with respect to the brain function of interest. An example of such measurements and processing is disclosed in U.S. Pat. No. 4,201,224 (hereby incorporated by reference in this application) and in the prior art discussed in it. Further background information can be found in U.S. Pat. Nos. 4,216,781; 4,279,258 and 4,188,956. In addition, machine-implemented techniques have been applied in seeking to find whether a significant difference exists between two sets of measurements taken from the same patient, such as in correlating the outputs of two electrodes placed in bilateral symmetry on the patient's head (e.g., U.S. Pat. No. 3,696,808), and carrying out a t-test to determine whether a statistically meaningful difference exists between the brainwaves generated in response to two different sets of stimuli (e.g., U.S. Pat. No. 3,901,215).

While in many cases it is important to know if a statistically and medically significant difference exists between the electrically measured brain function of a patient and the similarly measured brain function of a statistically and medically significant "normal" population, it has been discovered in the course of making this invention that in certain medical procedures it is additionally, or instead, advantageous to know if during the procedure certain changes have taken place in brain functions related to the particular procedure, as compared to the same functions of the same patient at a certain time before the procedure. As a nonlimiting example, in the case of a patient admitted for surgery in the course of which the regional blood (and hence oxygen) supply to the cortex, can be impaired, it has been discovered that it is advantageous and possible through this invention, to know not only the difference between the brain function associated with oxygen supply to the cortex as between this patient and a normal population but also changes in the function of the same patient as between a stable state with respect to this particular surgery (e.g. upon admission or upon administering anesthesia) and times during the surgery selected such that ample warning of a significantly reduced regional oxygen supply would be received before significant damage due to oxygen starvation can occur.

In accordance with a particular and nonlimiting example of the invention, brain functions of a patient which are selected for medical relevance to a planned medical procedure, are electrically measured at a time at which the patient is in a state selected for medical relevance to the procedure. In the nonlimiting example referred to immediately above, the medical procedure is the surgery, the state selected for medical relevance to the procedure is a state in which the patient is judged to be medically stable with respect to regional blood supply to the brain, e.g. soon after admission or soon after administration of anesthesia, and the brain functions selected for medical relevance to the procedure can be, e.g., the slow wave brain activity.

The measurements are processed to produce a self-norm comprising, for each brain function, a respective statistically and medically significant mean measurement and a respective statistically and medically significant standard deviation or variance measurement. In the same example, a sufficient number of measurements should be taken, in view of the anticipated variability of slow wave activity, so as to be able to derive a mean measurement which is not only statistically significant (as determined on the basis of known statistical criteria) but is also medically significant with respect to the known or perceived relationship between slow wave activity and regional oxygen supply to the cortex. Furthermore a sufficient number of measurements should be taken to allow not only the derivation of the desired mean but also the derivation of a similarly statistically and medically significant variance (or, in the simplified case, standard deviation).

After the procedure begins, the same brain functions of the same patient are electrically measured at each of a sequence of time intervals selected for medical relevance to the procedure. In the same nonlimiting example, the slow wave brain activity is measured during surgery at time intervals which are less than the duration of regional cortex oxygen starvation which could cause significant damage. For example, on the belief that significant damage occurs after 15–30 seconds of oxygen starvation, new measurements can be taken every five seconds.

Each new set of measurements is tested for statistically and medically significant change from the self-norm. In the nonlimiting example discussed here, each new set of measurements comprises slow wave measurements taken under measurement conditions sufficient to give a statistically and medically significant sample, and the desired test comprises testing the new set against the self-norm in a manner taking into account the statistically and medically significant mean and variance of the self-norm.

If such a change is detected, an indication is produced which conveys information not only as to the occurrence of the change but also as to the ascribed medical significance of the change itself and its persistence. In the example discussed here, the first indication of a change can result in a visual alert, a consecutive indication (i.e., a change persisting over two measurement intervals) can lead to an auditory alert for a possible emergency, a third consecutive indication can lead to an auditory and/or visual announcement of a possible emergency, and a fourth consecutive indication can lead to automatically initiated emergency procedures. If a change persists through two or three measurement intervals, but no change from the self-norm is found in the next interval, the system can go to the next lower level of alert.

In the case where two or more different brain functions are used in the self-norm and in the periodic measurements during the procedure, the change in each function from the corresponding component of the self-norm can be converted, in accordance with the invention, to a dimensionless probability of significant deviation, and these probabilities with respect to two or more brain functions can be combined, e.g. through vector addition of weighted or unweighted individual probabilities, into a single indication, e.g. in vector form, of a statistically and medically significant change from the self-norm.

As nonlimiting examples, the invention can be applied to monitoring a patient's brain functions against a self-norm in the case of surgical procedures which have the potential of affecting brainstem functions, or spinal cord functions, or thalamic cortical functions, surgical procedures which have the potential of affecting the EEG brain activity, surgical procedures which have the potential of affecting the ability to detect and process sensory stimuli, and medical procedures which comprise drug or other treatments having the potential of affecting electrically measurable brain function.

BRIEF DESCRIPTION OF THE DRAWINGS

FIG. 1 is a block diagram illustrating a system and a process embodying at least certain aspects of the invention.

DETAILED DESCRIPTION

Referring to FIG. 1 for an illustration of an exemplary process and system making use of at least some aspects of the invention, the portion comprising units 10–22 is for the purpose of taking measurements and establishing a self-norm before the medical procedure of interest commences, and the remainder is for the purpose of monitoring the procedure in order to detect, characterize and announce changes in the relevant brain function(s).

Unit 10 is a set of one or more input electrodes of the kind known in the art, whose output is amplified at 14 as also known in the art. However, the selection of which electrodes to use is made, in accordance with the invention, depending on the particular medical procedure of interest. Similarly, unit 12 comprises one or more devices for delivering sensory stimuli of the kind known in the art, but the selection and timing of the stimuli again depend, in accordance with the invention, on the particular medical procedure of interest. Still similarly, the outputs of electrode set 10, as amplified at 14, can be supplied to an optional frequency filter unit 16 which can selectively pass for any electrode only a waveform within a selected frequency window, using techniques known in the prior art. However, again the selection of a particular frequency window for a particular electrode depends on the particular medical procedure of interest. The output of unit 16, or the direct output of unit 14 is sampled for analog-to-digital conversion at 18 in a manner known in the art, at a sampling rate which is fixed or can be different as between different electrodes or as between different times. The timing and nature of any desired sensory stimuli are controlled by a unit 17 in the manner described in greater detail below. The same unit 17 can control the timing and nature of any frequency filter applied by unit 16, and can control the analog-to-digital conversion at unit 18, again as described in greater detail below.

At unit 20, a self-norm is constructed in accordance with the invention which is based on a suitable mean and variance (or standard deviation) of measurements for one or more brain functions. This self-norm is stored at 22 for later use as described below.

The self-norm is based on measurements made with electrode set 10 which (i) are taken at a time at which the patient is in a state selected for medical relevance to the planned medical procedure and (ii) are selected for medical relevance to the procedure. As a nonlimiting example, if the procedure is surgery which could impair regional blood supply to the cortex, the time for measurements useful to construct the self-norm is when the patient can be judged to be medically stable before the surgery commences, and the brain functions can be the slow wave activities at electrode locations which are known or at least believed to correlate to regional oxygen supply to the cortex. Enough measurements are taken and processed to allow for the derivation of a statistically and medically significant mean and variance for each brain function of interest. For statistical significance, the measurements should be sufficient in number and should be taken under measurement conditions which satisfy known statistical principles; for medical significance the measurements should be sufficient in number and should be taken under measurement conditions which allow for a reasonable expectation that the mean and variance correlate to the brain of physiological activity of interest.

For any particular, single brain function of interest, the mean is found in accordance with techniques known in the art, for example by finding the arithmetic mean through adding digitized waveforms for a succession of time intervals (each of which is longer than any periodically occurring event of interest), and dividing the sum by the number of time intervals. Similarly, the variance can be simplified to a standard deviation, which can be defined as the square root of the sum of the squared differences between the mean and the individual measurements, and can be found through techniques known in the art. In the alternative, the mean to be used can be weighted, i.e., it can be the sum of the individual measurements each weighted by a respective factor, this sum being divided by the sum of the factors (the arithmetic mean thus is a special case of the weighted mean—when each weighting factor is unity).

Once the mean and standard deviation for the one or more brain functions of interest have been derived and stored as discussed above, the actual monitoring of the patient's brain state during the medical procedure of interest can commence. To this end, at unit 24 in FIG. 1, a first set of measurements of the same one or more brain functions are taken over a time interval selected for medical relevance to the particular procedure. As one example, if the procedure has the potential of affecting regional oxygen supply to the cortex, and the monitored brain function is the slow wave circuitry, the first set of measurements can be taken within, say, five seconds from the first surgical procedure which can impair regional blood flow to the cortex, so that the sought test results can be available before significant damage due to oxygen starvation can occur. The set of measurements should be taken under conditions which can allow for a statistically and medically significant comparison with the self-norm. Thus, a sufficient number of samples should be taken to satisfy known statistical criteria taking into account the nature of the measurements, and sufficient measurements should be taken to satisfy known medical criteria for relevance of the measurements to the brain and/or physiological function of interest.

At unit 30 in FIG. 1, the set of measurements taken at 24 is tested for a statistically and medically significant change from the self-norm stored at 22. As one example in accordance with the invention, the test at 30 can involve finding the probabilities that the respective individual measurements taken at 24 are not significantly different from the mean stored at 22 when compared on the basis of the standard deviation also stored at 22. This type of test corresponds to finding the Z-transform discussed in said U.S. Pat. No. 4,201,224, which is incorporated by reference in this application. For example, if the set of measurements for a particular brain function taken at 24 is designated x, the self-norm mean for the same brain function stored at 22 is designated $\bar{x}$(self-norm), and the self-norm standard deviation for the same brain function stored at 22 is designated (self-norm), the z-transform Z can be derived in accordance with the relationship:

$$Z=[x-\bar{x}(\text{self-norm})]/\sigma(\text{self-norm}).$$

In the expression above, the quantity z can be a single measurement taken at unit 24 but, in the more typical case, it is the mean of several, repeated measurements, derived by using the same mean derivation technique as used to find the self-norm mean.

In the more typical case where several brain functions are of interest, and a respective mean and standard deviation for each is stored at 22, it can be advantageous not only to derive a measure, such as the Z-transform, indicative of a change from the self-norm as to each respective brain function, but also a composite measure which is a single quantity can indicate the combined change of all of the brain functions of interest. To this end, since each Z-transform quantity is already a probability measure rather than a measure expressed in the units of the particular measure of brain function a composite Z-transform can be derived which is the square root of the sum of the squares of the Z-transforms for the individual brain functions. Stated differently, the composite Z-transform Z(composite) can be derived in accordance with the following expression from the Z-transform quantities Z1, Z2, etc., which correspond to the individual brain functions 1, 2, 3, etc., of interest:

$$Z(\text{composite})=[(Z1)^2+(Z2)^2+\ldots+Z(N)^2]^{\frac{1}{2}}$$

If the Z-transform derived at unit 30 (whether composite or individual) is within a pre-stored threshold, then the test result is that there is no significant change from the self-norm, this information is conveyed to unit 26 and, under its control, unit 28 erases the set of measurements just taken at unit 24. If the Z-transform derived at 30 exceeds the threshold, then this is an indication of a significant change which is conveyed to unit 32 to initiate thereby a visual alert.

Whether or not the test at unit 30 has indicated a significant change from the self-norm, the next event is a repetition of the set of measurements at 24, under the control of unit 34, which unit tests the new, in this case second, set of measurements taken at unit 24 against the self-norm in the manner discussed above. If this test at unit 34 shows that there is no significant change as between the new measurements and the self-norm, unit 36 activates unit 38, to cancel the visual alert (in case the previous set of measurements led to a visual alert at unit 32) and unit 40 returns the system to unit 24, to take the next consecutive set of measurements.

In case unit 34 finds that a significant change exists as between the most recent set of measurements taken at unit 24 and the self-norm, unit 42 confirms that a second set of measurements has resulted in a finding of a significant change, and activates unit 44 to provide an auditory alert of a standby for a possible emergency.

The next operation is at unit 46, which causes unit 24 to take another set of measurements, and similarly tests that set of measurements against the self-norm. If no significant change is indicated, unit 48 cancels the alert produced by unit 44, and unit 40 causes unit 24 to take another set of measurements, to be similarly processed. If the test at unit 46 indicates a second consecutive significant change, unit 50 confirms the change and causes unit 52 to provide the next higher level of alert: an auditory-visual announcement of a possible emergency.

The next event is the operation of unit 54, whose function is to seek to clarify whether a true emergency exists. As one example, unit 54 can cause unit 24 to take another set of measurements but this time with a substantially increased sample size, e.g. doubled or trebled sample size so as to increase the reliability of the measurements, and unit 54 can then use the expanded set of measurements to perform the same type of test against the self-norm. As another example, unit 54 can rely on a new set of measurements from unit 24 which are the same in sample size as the previous ones, but can use a higher threshold in deciding whether the Z-transform from the most recent set of measurements is indicative of a significant change from the self-norm. If the different kind of test at unit 54 indicates that there is no significant change from the self-norm, control is transferred to units 56 and 58 which cancel the possible emergency announcement from unit 52, and transfer control to unit 40, which carries out its function described above.

If the test at unit 54 indicates that a significant change has persisted through four consecutive sets of measurements, the last of which is more stringent than the preceding ones, control is transferred to unit 60 which confirms the now more significant change, and activates unit 62 for initiation of emergency procedures the nature of which depends on the particular application of the invented system. Such emergency procedures can range from escalating the nature of the alarm given by the system to automatically increasing the blood or oxygen flow to a patient under surgery or automatically alerting personnel outside the operating room.

What I claim is:

1. A machine-implemented method for monitoring the occurrence and ascribed medical significance of changes in a patient undergoing a medical procedure relative to a prior state of the patient at a time selected for medical relevance to the planned procedure after administration of anesthesia, comprising:

electrically measuring brain functions of the patient which are selected for medical relevance to a medical procedure which the patient is to undergo, at said time at which the patient is in a state selected for medical relevance to the procedure, said selected state being after administration of anesthesia;

processing the measurements to produce a self-norm comprising, for each brain function, a respective statistically and medically significant mean measurement and a respective statistically and medically significant standard deviation or variance measurement;

electrically measuring the same brain functions of the same patient during the said procedure, at each of a sequence of time intervals selected for medical relevance to the procedure;

testing each new set of measurements for statistically and medically significant change from the self-norm;

converting each significant change to a dimensionless probability of significant deviation and combining at least two of the said probabilities through vector addition into a single vector-form indication of said medically significant change; and producing a tangible indication of the vector-form indication of the significant change, said tangible indication conveying information both as to the occurrence of a change and as to the ascribed medical significance of the change itself and the persistence of the change.

2. A method of monitoring the occurrence and ascribed medical significance of changes in a patient undergoing a medical procedure relative to a prior state of the patient at a time selected for medical relevance to the planned procedure, comprising the steps of:

selecting a patient state at a time after administration of anesthesia selected for medical relevance to a future medical procedure and electrically measuring brain functions of the patient which are also selected for medical relevance to the procedure;

processing the measurements to produce a self-norm comprising, for each brain function, a respective statistically significant mean measurement and a respective statistically significant standard deviation or variance measurement;

electrically measuring the same brain functions at each of a sequence of time interevals selected for medical relevance to the procedure, and testing each new set of measurements with respect to the self-norm to obtain significant changes;

converting each significant change to a dimensionless probability of significant deviation and combining at least two of the said probabilities through vector addition into a single vector-form indication of said medically significant change; and in case said vector-form indicates the occurrence of a change which is statistically significant and has an ascribed medical significance, producing a tangible indication of the change and, if the test based on the measurements taken in the subsequent time interval indicates that a significant change persists, escalating the nature and ascribed medical significance of the change tangible indication, with each consecutive test which indicates persistence of the change, up to a selected escalated level, but if a new test indicates the absence of a significant change, de-escalating the tangible indication to the one level per test, to a lower level tangible indication of change or to a tangible indication of no change, as the case may be.

* * * * *